United States Patent [19]

Baum

[11] Patent Number: 4,672,965

[45] Date of Patent: Jun. 16, 1987

[54] SURGICAL APPARATUS

[76] Inventor: Gilbert Baum, 152 Brire Ave., Scarsdale, N.Y. 10583

[21] Appl. No.: 641,376

[22] Filed: Aug. 16, 1984

[51] Int. Cl.⁴ ............................................. A61B 17/22
[52] U.S. Cl. ..................................... 128/305; 604/22
[58] Field of Search .................... 128/305, 303 R, 751, 128/318, 321; 604/22

[56] References Cited

U.S. PATENT DOCUMENTS

| 3,589,363 | 6/1971 | Banko et al. | 604/22 |
| 3,964,468 | 6/1976 | Schulz | 128/751 |
| 4,258,716 | 3/1981 | Sutherland | 128/321 |
| 4,508,532 | 4/1985 | Drews et al. | 604/22 |

OTHER PUBLICATIONS

Visitec Cystotomes (approx. May, 1984).
"Battery Powered Unit Aids Anterior Capsulectomy" IOL & Ocular Surgery News, Jul. 15, 1984.
SITE TRX TM Cutters, Ophthalmology, Times, Jul. 15, 1984.
Mendez, AM Intra-Ocular Implant Soc. J., vol. 10, Summer 1984, "Anterior Capsulotomy With Ultrasound Cystotome".
Cooper-Vision Systems Ocutome Pneumatic Intra-Ocular Scissors, Journal of Ocular Therapy & Surgery Jan.-Feb., 1984.

Primary Examiner—Gene Mancene
Assistant Examiner—David I. Tarnoff
Attorney, Agent, or Firm—David Aker

[57] ABSTRACT

An instrument similar in size and use to a cystotome, combining into a single instrument two knives which can be independently used so that the cutting surfaces of the knives can cut, at right angles to the surface to be incised, in either of two directions, one direction being at an angle with respect to the other direction. The knives are located at the ends of coaxially disposed elongate members formed from hypodermic needles. A first of the knives is guarded by the other knife until relative rotation of the needles brings the second knife into use. The inner one of the needles is connected to a hypodermic needle hub which in turn is connected to a hypodermic syringe, thus allowing fluids to be injected into or withdrawn from the surgical site. Apparatus suitable for causing vibration of the knives is included.

23 Claims, 5 Drawing Figures

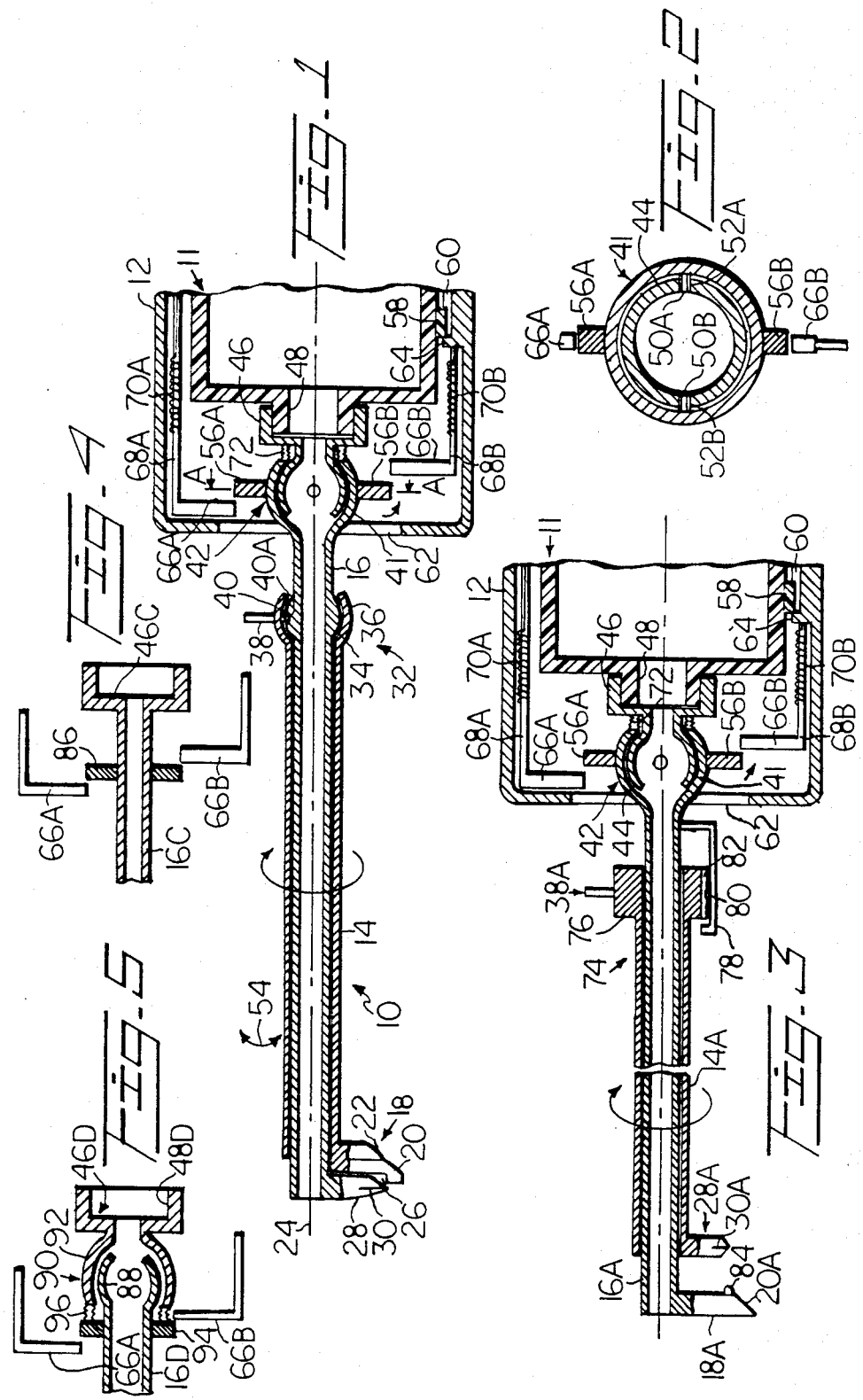

SURGICAL APPARATUS

FIELD OF THE INVENTION

This invention relates to surgical apparatus. More particularly, this invention relates to surgical apparatus suitable for incising tissue in a first direction and in a second direction, at an angle with respect to the first direction where the incisions are made in a region of very limited volume such as in parts of the eye or in regions of the nervous system.

BACKGROUND OF THE INVENTION

In the past of variety of different devices such as miniature knives, scissors and needles have been used to make surgical incisions in regions of limited volume such as in parts of the eye.

As an example, modern cataract removal techniques currently employ extra capsular cataract extraction. An essential step in this surgical procedure is the proper incision of the anterior lens capsule. This incision is usually carried out through a 3.0 mm to 4.0 mm limbal incision, to retain the closed condition of the eye. This small incision restricts the motion of the knife so that the leading edge of the cutting surface is rarely at right angles to the surface to be cut. To deal with this problem an "can opener" type of incision has been developed where multiple punctures are made into the anterior lens capsule. Then, the central portion of the anterior lens capsule is torn away from the peripheral portion. This results in a frayed edge with capsule strands which may complicate the remainder of the surgical procedure.

In addition, passage into and out of the anterior chamber represents a threat to the corneal integrity because of possible damage to Descement's membrane, as well as the corneal endothelium. There is also the possibility of a collapse of the anterior chamber each time an instrument, such as a sharp needle is withdrawn. Such a collapse can prove inimical to the iris, cornea and the lens.

SUMMARY OF THE INVENTION

The present invention advantageously combines two knives in a single instrument similar to a cystotome so that only a single entry and exit into a region in which surgery is being performed (such as the anterior chamber of the eye), is necessary to make surgical incisions, some of which are at an angle with respect to other of the incisions.

The present invention comprises first and second coaxially disposed elongate members, each member having a cutting means at an end thereof. The cutting means are located in close proximity to one another, one of the cutting means being for cutting in a first direction and the other being for cutting in a second direction at an angle with respect to the first direction. A positioning means, which is preferably a ball and socket joint, permits the surgeon to cause relative axial rotation of one elongate member with respect to the other elongate member while permitting either limited or not relative axial displacement between the elongate members. Thus the cutting means are not permitted to come into contact with one another, but can be moved rotationally past one another. A recess may be provided in a first of the cutting means to receive at least a portion of the second cutting means so that the first cutting means acts as a guard for the second cutting means. Alternatively, one of the cutting means may be configured with a protrusion which acts as a guard. Vibration means are provided to cause the first and second cutting means to vibrate.

The first and second elongate members are preferably hypodermic needles. An inner one of the members may have its end, opposite the end having a respective cutting means, configured as the socket of a second ball and socket joint. A hypodermic needle hub is configured with a first portion which connects to a hypodermic syringe and a second position which serves as the ball of the second ball and socket joint. The syringe permits the introduction and removal of fluid from the surgical site. A pivot means which permits the socket to pivot with respect to the ball of the second ball and socket joint but prevents relative axial rotation of the ball with respect to the socket is provided.

A housing which receives a hypodermic syringe connected to the needle hub and the second ball and socket joint is also provided. Motive means are provided to cause the socket of the second ball and socket joint to oscillate or vibrate with respect to the ball of the second ball and socket joint, thus causing the first and second cutting means to undergo vibration.

BRIEF DESCRIPTION OF THE DRAWINGS

A further understanding of the functions and advantages of the present invention will become apparent by reference to the following drawings in which:

FIG. 1 is an enlarged substantially cross sectional view of a first embodiment of the invention.

FIG. 2 is a further enlarged, partial cross sectional view taken along line A—A of FIG. 1.

FIG. 3 is an enlarged substantially cross sectional view of a second embodiment of the invention.

FIG. 4 is a fragmentary enlarged cross sectional view illustrating an alternative vibration producing arrangement.

FIG. 5 is a fragmentary enlarged cross sectional view illustrating a further vibration producing arrangement.

DETAILED DESCRIPTION OF THE PREFERRED EMBODIMENTS

Referring to the drawings, in which like parts are referred to by like reference numerals, there is shown in FIG. 1 an assembly including a basic surgical apparatus 10 and a hypodermic syringe 11 in a housing 12.

Apparatus 10 includes a first outer elongate member 14 and a second inner elongate member 16 which are coaxially disposed with respect to one another. The inner elongate member 16 may be of the same diameter and wall thickness as a 26 gauge hypodermic needle, the outer member 14 then being of the same diameter and wall thickness as a 21 guage needle. Members 14 and 16 can be formed from such needles. The use of such hollow tubes 14 and 16 permit the introduction and removal of fluids from the surgical site by means of hypodermic syringe 11. Outer member 14 is preferably approximately 1.6 cm long, while inner member 16 is approximately 0.64 cm longer.

A first cutting means 18 having a knife edge 20 and a guard 22 is disposed at an end of member 14. Cutting means 18 is shaped from and positioned with respect to outer member 14 so that knife edge 20 produces an incision in a direction parallel to longitudinal axis 24 of elongate members 14 and 16 (which axis is also the longitudinal axis of the apparatus). Such an incision, made in a direction toward the surgeon is referred to herein as a vertical incision and cutting means 18 as the vertical knife. Typically, cutting means 18 extends approximately 0.12 cm radially outward from the outer wall of member 14, with knife edge 20 having an extent in the radial direction of approximately one third that dimension.

Guard 22 has a rounded off blunt shape in the direction in which cutting means 18 incises the tissue and is therefore useful in that it aids the surgeon in controlling the depth of the cut and assures that only the portion of cutting means 18 (knife edge 20) which can incise the tissue comes in contact with the tissue to be incised.

A recess 26 is provided in cutting means 18 for receiving at least a part of a second cutting means 28 dispsed at the end of elongate member 16. Cutting means 28 thus extends radially from axis 24 by a distance less than that of cutting means 18. Cutting means 28 has a double knife edge 30 oriented so as to incise tissue in a direction at an angle with respect to knife edge 20, the angle being ninety degrees in FIG. 1. An incision made in such a direction is referred to herein as a horizontal incision and cutting means 28 is referred to as a horizontal knife. Due to the double edge 30, incisions can be made either to the left or to the right as viewed by the surgeon, depending on the relative rotational orientation of cutting means 28 with respect to cutting means 18 as noted below.

Both cutting means 18 and 28 are formed by conventional metal working techniques from the ends of members 14 and 16. Appropriate forming and/or tempering steps are used, as required by the material to produce sharp cutting edges.

A positioning means in the form of a ball and socket joint 32 allows members 14 and 16 to be rotated with respect to one another so that cutting means 28 is guarded in recess 26 of cutting means 18 in a first relative rotational position of members 14 with respect to member 16 and exposed for use in incising tissue in the horizontal direction in a second relative rotational position of member 14 with respect to member 16. However, ball and socket joint 32 does not permit relative axial displacement of members 14 and 16. Ball and socket joint 32 is comprised of a ball 34 surrounding and fixed with respect to member 16 and a socket 36 fixed to the end of member 14 opposite the end on which cutting means 18 is disposed.

A cylindrical handle 38 is affixed to and extends radially from socket 36 allowing the surgeon to rotate member 14 with respect to member 16, thus either guarding or exposing knife edge 30 of cutting means 28.

While frictional forces between ball 34 and socket 36 might well be sufficient to maintain a fixed rotational relationship between members 14 and 16, it is also possible to provide a locking arrangement, such as a locking protrusion 40 fixedly secured to the internal surface of socket 36. Ball 34 would then have a series of circumferentially arranged notches such as 40A to accept protrusion 40, to positively secure the relative rotational relationship between members 14 and 16. Protrusion 40 may be formed of a relatively flexible and resilient material so that it can deform slightly during motion from notch to notch and then returns to its original shape to drop into one of the notches. Preferably a total of five notches would be provided allowing protrusion 40 to be secured at positions of 0 degrees (as shown in FIG. 1) ±45 degrees and ±60 degrees, all positions other than 0 degrees permitting knife edge 30 of cutting means 28 to be exposed to incise the tissue in the horizontal direction.

The end of member 16 remote from cutting means 28 is formed as the socket 41 of a second ball and socket joint 42. The ball 44 of ball and socket joint 42 is a part of a hypodermic needle hub 46 suitable for coupling, preferably by friction, to the coupling portion 48 of hypodermic syringe 11.

As shown in FIG. 2 socket 41 is configured with pivot means or protrusions 50A and 50B extending into depressions or holes 52A and 52B in ball 44. These protrusions allow the assembly 10 to pivot with respect to the syringe 11, but do not permit relative axial rotation of member 16 with respect to syringe 11.

A means of connection including a pivot is used so that the entire assembly 10 can be caused to undergo small amplitude vibration or oscillation in the direction represented by arrow 54. To this end, circumferentially disposed magnetic members 56A and 56B which may be made of a high permeability magnetic material are fixed to the outside of socket 41. Syringe 11 is configured with an alignment means or rotational locating protrusion 58 which fits into a locating aperture such as a slot 60 in housing 12, when the combination of surgical assembly 10 and syringe 11 is caused to slide from the right in FIG. 1 into housing 12, surgical assembly 10 then extending through opening 62 of housing 12. When protrusion 58 contacts shoulder 64 at the end of slot 60, magnetic members 56A and 56B are disposed opposite electromagnetic poles 66A and 66B associated with magnetic cores 68A and 68B upon which coils 70A and 70B respectively are wound.

Coils 70A and 70B are excited by a low voltage high current source (not shown) of the type suitable for use in operating rooms. This source may be placed in a housing (not shown) separate and apart from housing 12 and connected to housing 12 by suitable electrical conductors. An alternating current of relatively low frequency is used to produce the small amplitude vibration mentioned above. Typically vibration amplitude is limited so as to be in the range of approximately 0.1 to 0.2 mm at knife edges 20 and 30. This vibration greatly facilitates the cutting action of knife edges 20 and 30 when incisions are made.

Due to the need to permit the vibratory motion, it is not possible to assure a liquid tight seal of socket 41 to ball 44. Therefrom a sealing means such as an elastomeric bellows 72 is provided between socket 41 and needle hub 46.

FIG. 3 illustrates an alternate embodiment of the invention in which horizontal knife 28A having double knife edge 30A is attached to outer elongate member 14A and vertical knife 18A having knife edge 20A is attached to inner elongate member 16A. Instead of a ball and socket joint, positioning means 74 comprising a radially extending annular member 76 fixedly secured to the end of member 14A at the end opposite that of horizontal knife 28A. Position limiting bracket 78, fixedly secured to member 16A, contacts the radially extending walls of annular member 76 to allow limited relative axial motion of member 14A with respect to member 16A.

To secure the relative rotational relationship between members 14A and 16A a locking protrusion 80 is provided on the surface of bracket 78 facing annular member 76. A series of longitudinally extending circumferentially arranged slots such as 82 to receive protrusion 80 are provided on annular member 76, thus rotationally securing member 14A with respect to member 16A at a plurality of positions in a manner similar to that described above with respect to protrusion 40 of FIG. 1. A radially extending cylindrical handle 38A is provided to allow manipulation of annular member 76.

Bracket 78 is configured so that the relative axial motion of member 14A with respect to member 16A is limited so that vertical knife 18A and horizontal knife 28A do not contact one another. Further a guard 84 which is at a radial distance from axis 24A of the apparatus greater than the radial extent of horizontal knife 28A but less than that of vertical knife 18A is provided. Guard 84 protrudes from knife 18A in a direction parallel to axis 24A and guards double knife edge 30A when it is in its position closest to vertical knife 18A. Further, it acts as a depth guage for knife edge 20A.

FIG. 4 illustrates an alternative arrangement for producing vibration of the cutting knives. An annular magnetic member 86 is affixed to the outside of an inner needle or elongate member 16C which is integral with needle hub 46C. Magnetic poles 66A and 66B then act in a manner similar to that illustrated in FIG. 1, but cause flexing of inner member 16C, which must be formed from a suitable material so that such flexing does not cause work hardening and fracture of member 16C during the surgical procedure.

FIG. 5 illustrates a further arrangement for producing vibration of the cutting knives. Inner elongate member 16D has an end formed as a ball 88 of ball and socket joint 90. Needle hub 46D has a first portion 48D for fitting to a syringe and a second portion 92 formed as the socket of ball and socket joint 90. An annular magnetic number 94 is fixedly attached to inner elongate member 16D and is acted upon by magnetic poles 66A and 66B. A liquid seal, such as an elastomeric bellows 96 is provided between socket 92 and magnetic number 94. Bellows 96 may itself act as a pivot means, while preventing rotation of inner elongate member 16D with respect to needle hub 46D due to attachment to both magnetic member 94 and socket 92.

It will be understood that magnetic members 86 or 94 could also be affixed to the outer one of the elongate members.

The instrument according to this invention is used for cataract extraction in a manner identical to that used with present day cystotome techniques. Thus, a 3-4 mm limbal incision is made. The instrument is configured, by using the positioning means for causing relative rotation of the inner and outer elongate members, so that the vertical knife covers (acts as a guard for) the horizontal knife and and the instrument is then inserted into the eye with both knives parallel to the plane of the iris upon insertion. After the cystotome enters the anterior chamber the entire assembly is rotated 90 degrees about its longitudinal axis so that both knives face downward toward the lens. Medial and lateral vertical incisions into the lens capsule is then made using the vertical knife, thus forming two parallel incisions. The vertical knife is then rotated 45 to 60 degrees without rotating the horizontal knife thus exposing the horizontal knife. The horizontal knife is thus retained in a plane perpendicular to the plane of the iris. The horizontal knife is then used to make incisions which connect the lateral and medial capsular incisions at both the lower and upper poles of the lens, the paths of the incisions then being a rectangle in a plane parallel to the iris. The vertical knife is then rotated down 30 degrees and both the horizontal and vertical knives are used as points of forceps to rotate and free the lens nucleus prior to its expression. After the lens nucleus has been freed the vertical knife is rotated so that the horizontal knife is again guarded. Then the entire instrument is rotated so that the knives again lie in a plane parallel to the iris and the entire instrument is withdrawn from the eye.

In summary, the apparatus of the present invention produces smooth linear incisions which do not have frayed edges. This instrument retains the size of existing cystotomes but combines into a single instrument two knives which can be independently used so that the cutting surfaces can cut, at right angles to the surface to be incised, in either a horizontal or vertical direction at maximal cutting efficiencies. Another advantage of this apparatus is that is is virtually identical in size, shape and form to existing cystotomes so that ocular surgeons are familiar with this type of instrumentation and its use. The use of this instrument merely entails that the surgeon choose whether he wishes to use the vertically cutting knife or the horizontally cutting knife. Knife selection is achieved by a simple 60 degrees rotation of the vertical knife which shifts the vertical knife from its cutting position and exposes the horizontally cutting knife. The vertical cutting knife can be rotated to either side (i.e. right or left) of the horizontal knife.

Various modifications of the invention other than those illustrated herein will become apparent to those skilled in the art. For example, the outer elongate member may be made of a relatively flexible material so that it can change its shape and will rotate around the inner elongate member if the inner elongate member is bent to assume a shape for a particular surgical procedure. Pivot means other than those shown herein may be devised. Finally as is apparent from the above description, either the outer or inner elongate member may support either the vertical or horizontal knives. All such modifications are intented to fall within the scope of the appended claims.

I claim:

1. A surgical apparatus for incising tissue, said apparatus comprising:
   a first elongate member;
   a first cutting means located at a first end of said first elongate member, said first cutting means being for cutting through the tissue in either one of a first direction parallel to said first elongate member or a second direction at an angle with respect to said first direction;
   a second elongate member coaxially disposed with respect to said first elongate member;
   a second cutting means located at an end of said second elonagate member, said second cutting means being for cutting in the other of said first and second directions;
   said first elongate member and said second elongate member being configured so that one of said first elongate member and said second elongate member surrounds a substantial portion of another of said first elongate member and said second elongate member, and so that said first cutting means and said second cutting means are in close proximity to each other; and
   a positioning means for causing relative axial rotation of said first elongate member with respect to said second elongate member while permitting at most only limited axial displacement of said first elongate member with respect to said second elongate member so that said first cutting means and said second cutting means can be moved rotationally past one another.

2. The surgical apparatus of claim 1 further comprising vibrating means for causing said first cutting means and said second cutting means to undergo vibration.

3. The surgical apparatus of claim 2 in which said vibrating means comprises a magnetic member affixed to one of said first and second elongate members, and magnetic field means for producing vibratory forces on said magnetic member.

4. The surgical apparatus of claim 1 in which said first cutting means is for cutting in a direction parallel to a longitudinal axis of said apparatus.

5. The surgical apparatus of claim 4 in which said first cutting means extends radially from said longitudinal axis of said apparatus for a first distance and said second cutting means extend radially from said longitudinal axis of said apparatus for a second distance, said first distance being greater than said second distance.

6. The surgical apparatus of claim 5 in which said first cutting means is configured with a recess into which at least a portion of said second cutting means is received, so that said first cutting means acts as a guard for said second cutting means.

7. The surgical apparatus of claim 5 further comprising a guard extending from said first cutting means in a direction parallel to said longitudinal axis of said apparatus at a third radial distance from said longitudinal axis, said third radial distance being less than said first distance and greater than said second distance.

8. The surgical apparatus of claim 1 in which said first elongate member and said second elongate member are tubes.

9. The surgical apparatus of cliam 1 in which said first elongate member and said second elongate member are hypodermic needles.

10. The surgical apparatus of claim 1 in which said angle is ninety degrees.

11. The surgical apparatus of claim 1 in which said positioning means comprises a ball and socket means, an outer one of said elongate members being connected to a socket of said ball and socket means and an inner one of said elongate members being connected to a ball of said ball and socket means.

12. The surgical apparatus of claim 11 in which said positioning means further comprises a handle extending radially outward from said ball.

13. The surgical apparatus of claim 1 in which said positioning
means comprises:
a radially outwardly extending annular member connected to an outer one of said first elongate member and said second elongate member at a position removed from the end of said outer elongate member having a respective one of said cutting means; and
a position limiting means for contacting said annular member so as to permit only limited axial movement of said annular member with respect to an inner one of said first elongate member and said second elongate member.

14. The surgical apparatus of claim 13 in which said position limiting means is a bracket having a first portion extending radially from said inner elongate member, a second position extending parallel to a longitudinal axis of said inner elongate member, and a third portion extending radially inward toward said inner elongate member, said first portion and said third portion being for contacting radial walls of said annular member.

15. The surgical apparatus of claim 13 further comprising a handle extending radially outward from said annular member.

16. The surgical apparatus of claim 1 in which an inner one of said first elongate member and said second elongate member is a hypodermic needle and has a second end which is formed as a socket of a ball and socket joint, said second end being opposite the end at which its respective cutting means is located, the apparatus further comprising a hypodermic needle hub, the hub having a first portion for fitting to a hypodermic syringe and a second portion formed as the ball of said ball and socket joint.

17. The apparatus of claim 16 further comprising sealing means for forming a liquid tight seal between said socket and said needle hub.

18. The apparatus of claim 16 further comprising a hypodermic syringe fitted to said hub of said hypodermic needle.

19. The apparatus of claim 18 further comprising a housing for receiving said hypodermic syringe, said needle hub and said ball and socket joint; pivot means for permitting a pivotal motion of said socket with respect to said ball while preventing rotation of said socket with respect to said ball, and motive means for causing said socket to undergo an oscillatory motion about said pivot means.

20. The apparatus of claim 19 in which said motive means comprises armature means affixed to said socket and field means affixed to said housing.

21. The apparatus of claim 20 further comprising alignment means attached to said hypodermic syringe, said alignment means being for fitting into a locating aperture in said housing to rotationally align said field means and said armature means.

22. The surgical apparatus of claim 1 in which an inner one of said first elongate member and said second elongate member is a hypodermic needle and has a second end which is formed as the ball of a ball and socket joint, said second end being opposite the end at which its respective cutting means is located, the apparatus further comprising a hypodermic needle hub, the hub having a first portion for fitting to a hypodermic syring and a second portion forming as the socket of said ball and socket joint.

23. The surgical apparatus of claim 1 further comprising a hypodermic needle hub, pivot means for securing an inner one of said first elongate member and said second elongate member to said hypodermic needle hub, and sealing means to provide a liquid tight seal between said inner elongate member and said needle hub.

* * * * *